United States Patent [19]

Hoornaert et al.

[11] Patent Number: 5,001,159
[45] Date of Patent: Mar. 19, 1991

[54] N-AMINOBUTYL-N-PHENYLARYLAMIDE COMPOUNDS AND THEIR APPLICATION IN THERAPY

[75] Inventors: Christian Hoornaert, Paris; Jean-Claude Muller, Morsang Sur Orge; Nigel Beeley, Combs La Ville, all of France

[73] Assignee: Synthelabo, Paris, France

[21] Appl. No.: 517,419

[22] Filed: May 2, 1990

Related U.S. Application Data

[63] Continuation of Ser. No. 218,873, Jul. 14, 1988, abandoned.

[30] Foreign Application Priority Data

Jul. 16, 1987 [FR] France .................... 87 10026

[51] Int. Cl.⁵ ............... C07D 103/26; A61K 31/165
[52] U.S. Cl. .................... 514/619; 514/613; 514/617; 514/464; 514/522; 564/166; 564/167; 564/168; 564/180; 549/441; 558/415
[58] Field of Search ............ 558/415; 549/441; 564/166, 167, 168, 180; 514/464, 522, 613, 617

[56] References Cited

U.S. PATENT DOCUMENTS 3,573,320 3/1971 Jansen et al. ............... 260/305
3,818,021 6/1974 Thuillier ................... 260/295

FOREIGN PATENT DOCUMENTS 1232787 3/1971 United Kingdom ............. 548/368
1282600 7/1972 United Kingdom ............. 260/295

OTHER PUBLICATIONS

Chemical Abstracts, vol. 103, No. 1, July. 1988, p. 538 No. 5978e.
Chemical Abstracts, vol. 82, No. 1, 6 Jan. 1975, pp. 366–367, Nr. 4223r.

Primary Examiner—Frederick E. Waddell
Assistant Examiner—Zinna Northington-Davis
Attorney, Agent, or Firm—Fleit, Jacobson, Cohn, Price, Holman & Stern

[57] ABSTRACT

A compound of formula (I)

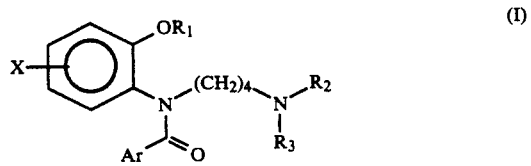

in which:

X denotes hydrogen, a halogen, a trifluoromethyl group, a $C_1$–$C_4$ alkyl group or a $C_1$–$C_4$ alkoxy group;

$R_1$ denotes a linear or branched $C_2$–$C_8$ alkyl group, a $C_3$–$C_5$ cycloalkyl group or a cycloalkylmethyl group in which the cycloalkyl moiety has from 3 to 5 carbon atoms;

$R_2$ denotes hydrogen or a $C_1$–$C_4$ alkyl group;

$R_3$ denotes hydrogen, a $C_1$–$C_4$ alkyl group, an optionally substituted phenylalkyl group or a pyridylalkyl group;

or $R_2$ and $R_3$ denote, together with the nitrogen to which they are attached, a pyrrolidinyl, piperidyl, morpholinyl, perhydrothiazinyl, piperazinyl or 4-methylpiperazinyl ring; and Ar denotes a phenyl group, optionally having from one to three substituents, each of which is, independently, a halogen or a $C_1$–$C_4$ alkyl, $C_1$–$C_4$ alkoxy, trifluoromethyl, nitro or cyano group, or Ar denotes a naphthyl, pyridyl, quinolinyl or isoquinolinyl group;

or a pharmacologically acceptable acid addition salt thereof.

17 Claims, No Drawings

N-AMINOBUTYL-N-PHENYLARYLAMIDE COMPOUNDS AND THEIR APPLICATION IN THERAPY

This application is a continuation of application Ser. No. 218,873, filed July 14, 1988, abandoned.

The present invention relates to N-aminobutyl-N-phenylarylamide derivatives, their preparation and their application in therapy.

The present invention provides a compound of formula (I)

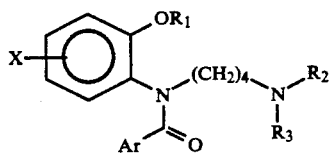
(I)

in which:

X denotes hydrogen, a halogen, a trifluoromethyl group, a $C_1-C_4$ alkyl group or a $C_1-C_4$ alkoxy group;

$R_1$ denotes a linear or branched $C_2-C_8$ alkyl group, a $C_3-C_5$ cycloalkyl group or a cycloalkylmethyl group in which the cycloalkyl moiety has from 3 to 5 carbon atoms;

$R_2$ denotes hydrogen or a $C_1-C_4$ alkyl group;

$R_3$ denotes hydrogen, a $C_1-C_4$ alkyl group, an optionally substituted phenylalkyl group or a pyridylalkyl group;

or $R_2$ and $R_3$ denote, together with the nitrogen to which they are attached, a pyrrolidinyl, piperidyl, morpholinyl, perhydrothiazinyl, piperazinyl or 4-methylpiperazinyl ring; and Ar denotes a phenyl group, optionally having from one to three substituents, each of which is, independently, a halogen or a $C_1-C_4$ alkyl, $C_1-C_4$ alkoxy, methylenedoxy trifluoromethyl, nitro or cyano group, or Ar denotenotes a naphthyl, pyridyl, quinolinyl or isoquinolinyl group.

Preferred compounds are those in which $R_1$ denotes an isobutyl group and Ar denotes a substituted phenyl group, and those in which X denotes hydrogen and $R_2$ denotes a methyl group. Especially preferred compounds are those in which $R_3$ denotes a methyl group and Ar denotes a. 2,3-dimethylphenyl, 3-trifluoromethylphenyl, 3-nitrophenyl or 2-methoxy-3-nitrophenyl group; those in which $R_3$ denotes a 2-(3-methoxyphenyl)-ethyl, 2-(3,4-dimethoxyphenyl)ethyl or 2-(3-pyridyl)ethyl group and Ar denotes a 3-trifluoromethylphenyl group; and those in which $R_1$ denotes a 2-(3,4-dimethoxyphenyl)ethyl group and Ar denotes a 2-methyl-3-nitrophenyl group.

The present invention provides a process for preparing a compound of formula (I), which comprises acylating a diamine of formula (II)

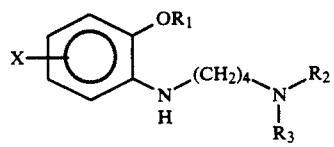
(II)

in which X, $R_1$, $R_2$ and $R_3$ are as defined above, with an acid chloride of formula (III)

ArCOCl (III)

in which Ar is as defined above.

The acylation is preferably carried out in the cold, in a solvent and in the presence of a base such as potassium carbonate.

The diamine of formula (II) may be obtained, for example, by a process as illustrated in each of the Schemes 1a and 1b below.

According to Scheme 1a, a primary benzenamine of formula (IV), in which X and $R_1$ are as defined above, is first acylated with 4-chlorobutanoyl chloride of formula (V), generally in the cold and in the presence of a base. The amide of formula (VI) thereby obtained is then reacted with an amine of the formula (VII), in which $R_2$ and $R_3$ are as defined above, generally in a solvent such as acetonitrile, dimethylformamide, ethanol or tetrahydrofuran, preferably in the heated state, in the presence of potassium iodide, a phase transfer agent such as tetrabutylammonium iodide and a base such as potassium carbonate.

Finally, the amide of formula (VIII) thereby obtained is reduced, using, for example, lithium aluminium hydride or diborane or an alkali metal borohydride, preferably in a solvent in the heated state.

According to Scheme 1b, an acetamide of formula (IX), in which X and $R_1$ are as defined above, which may itself be prepared in a known manner from a benzenamine of formula (IV) is reacted with 1-bromo-4-chlorobutane of formula (X), generally in the cold, in an aprotic polar solvent such as dimethylformamide, dimethyl sulphoxide or acetone, in the presence of a base such as sodium hydride, potassium hydroxide or potassium carbonate. The compound of the formula (XI) thereby obtained is then reacted with an amine of formula (VII), in which $R_1$ and $R_3$ are as defined above, in a manner similar to that described above in relation to the reaction between the amide of formula (VI) and the amine of formula (VII).

A compound of formula (XII) is thereby obtained, which can be converted to the diamine of formula (II), for example, by adding water and a base such as potassium tert-butylate or potassium hydroxide, in the heated state and in a solvent such as tetrahydrofuran or dioxane.

The present invention provides another process for preparing a compound of formula (I) which comprises reacting a compound of formula (XIV)

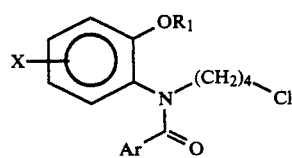
(XIV)

in which X, $R_1$ and Ar are as defined above with an amine of formula (VII)

HNR$_2$R$_3$ (VII)

in which $R_2$ and $R_3$ are as defined above.

The conditions of reaction are preferably similar to those described above in relation to the reaction between the amide of formula (VI) and the amine of formula (VII).

The compound of formula (XIV) may be prepared, for example, by reacting a compound of formula (XIII)

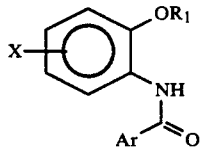 (XIII)

wherein X, $R_1$ and Ar are as defined above with 1-bromo 4-chlorobutane.

The reaction conditions are generally similar to those described above in relation to the reaction between the acetamide of formula (IX) and 1-bromo-4-chlorobutane.

The compound of formula (XIII) may, for example, be prepared by acylating a compound of formula (IV)

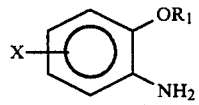 (IV)

in which X and $R_1$ are as defined above with an acid chloride of formula (III)

ArCOCl (III)

in which Ar is as defined above.

This reaction is generally carried out at a temperature of from $-10°$ to $+30°$ C. in a solvent such as dichloromethane, ether or tetrahydrofuran, and in the presence of a base such as potassium carbonate, triethylamine or 4-(dimethylamino)pyridine.

The benzenamine of formula (IV) may be obtained according to various known methods.

It is possible, for example, to alkylate an N-(2-hydroxyphenyl)acetamide bearing a substituent X as defined above to obtain the corresponding N-(2-alkoxyphenyl)acetamide, and then to decompose the latter compound to the benzenamine of formula (IV) by hydrolysis.

It is also possible to react a 2-halonitrobenzene bearing a substituent X as defined above with an alcohol of formula R OH to obtain the corresponding 2-alkoxynitrobenzene, and then to reduce the latter compound to the benzenamine of formula (IV).

Finally, it is possible to alkylate a 2-nitrophenol bearing a substituent X, as defined above to obtain the corresponding 2-alkoxynitrobenzene and to reduce the latter compound to the benzenamine of formula (IV).

Scheme 1a

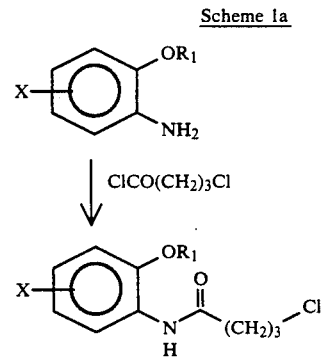

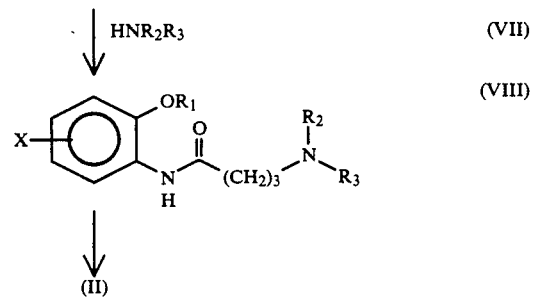

-continued
Scheme 1a

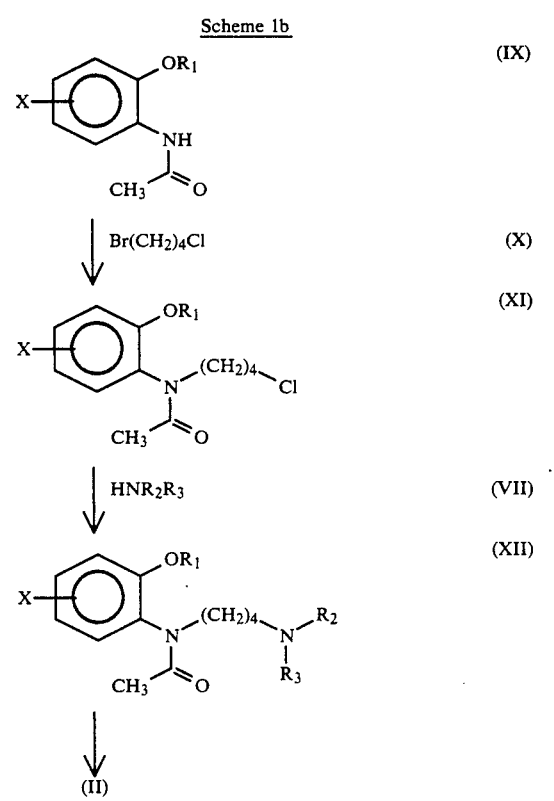

The Examples which follow illustrate in detail the preparation of a few compounds according to the invention. The microanalyses and IR and NMR Spectra of the products obtained confirm their structures.

The numbers appearing in brackets in the titles of the Examples correspond to those in the table given later.

EXAMPLE 1

(Compound No. 23)

N-[4-(Dimethylamino)butyl]-N-[2-(2-methylpropoxy)-phenyl]-2,5-dichlorobenzamide fumarate (a)

4-Chloro-N-[2-(2-methylpropoxy)phenyl]butanamide

A solution of 44 ml of 4-chlorobutyryl chloride in 350 ml of ether is added dropwise to a suspension of 60 g of 2-(2-methylpropoxy)benzenamine and 199 g of potassium carbonate in 500 ml of ether, cooled in an icebath, and the mixture is stirred overnight at room temperature. The mixture is filtered and the filtrate washed successively with 200 ml of 1 N sodium hydroxide, three times 100 ml of water and 100 ml of saturated sodium chloride solution. The ethereal solution is dried over magnesium sulphate and the solvent evaporated off. 85.8 g of syrupy product are collected, and used without further treatment in the following stage.

(b)
4-(Dimethylamino)-N-[2-(2-methylpropoxy)phenyl]-butanamide

The above product is dissolved in 620 ml of acetonitrile, and 126 g of dimethylamine hydrochloride, 51.5 g of potassium iodide, 107 g of potassium carbonate and 5.7 g of tetra-n-butylammonium iodide are added. The mixture is heated to reflux for 7 h and filtered, washing the solid with acetonitrile, and the filtrate is evaporated. The residue is taken up with 1,000 ml of ether and 500 ml of 1 N sodium hydroxide. The organic phase is separated off, washed with saturated sodium chloride solution, dried over magnesium sulphate and evaporated under vacuum. 45 g of crude product are obtained.

By extracting the aqueous phases three times with 200 ml of dichloromethane, a further 19 g of product, which are added to the 45 g already isolated, are obtained after drying and evaporation. The combined product is purified by formation of the corresponding hydrochloride and recrystallization. After liberation of the base by treatment with a base, 52 g of syrupy product are collected, and this is used without further treatment in the following stage.

(c)
N,N-Dimethyl-N'-[2-(2-methylpropoxy)phenyl]-1,4-butanediamine 52 g of the above product are dissolved in 300 ml of tetrahydrofuran, and the solution obtained is added dropwise to a suspension of 14 g of lithium aluminium hydride in 600 ml of tetrahydrofuran, cooled in an icebath.

The mixture is then heated to reflux for 3 h, allowed to cool and treated with a solution of 19 g of sodium hydroxide in 25 ml of water.

The mixture is diluted with 500 ml of ethyl acetate and filtered over magnesium sulphate. The filtrate is evaporated and the residue distilled under vacuum, which gives 31.3 g of product.

Boiling point: 118°–124° C. at 20 Pa (0.15 mmHg).

(d)
N-[4-(Dimethylamino)butyl]-N-[2-(2-methylpropoxy)-phenyl]-2,5-dichlorobenzamide A solution of 2.3 g of 2,5-dichlorobenzoyl chloride in 30 ml of ether is added dropwise to a mixture of 2.4 g of the above compound, 4 g of potassium carbonate and 30 ml of ether.

The mixture is stirred overnight and 100 ml of water and 40 ml of ether are then added. The organic phase is separated off, washed three times with 50 ml of water and then 50 ml of saturated sodium chloride solution, dried over magnesium sulphate and evaporated under vacuum. After purification by chromatography on a silica column, 3.2 g of syrupy product are obtained.

3 g of this are dissolved in methanol, 0.8 g of fumaric acid is added, the solvent is driven off under vacuum and the residue is recrystallized in ethyl acetate. 2.9 g of fumarate are obtained in the form of a white powder. Melting point: 130° C.

EXAMPLE 2

(Compound No. 2)

N-[4-(Dimethylamino)butyl]-N-[2-(2-methylpropoxy)-phenyl]-3-(trifluoromethyl)benzamide hydrochloride (a)
N-(4-Chlorobutyl)-N-[2-(2-methylpropoxy)phenyl]acetamide To a suspension of 10.3 g of lithium hydride (at a concentration of 50% in oil) in 100 ml of dimethylformamide, cooled in an ice-bath, there are added dropwise 35.6 g of N-[2-(methylpropoxy)phenyl]acetamide dissolved in 70 ml of dimethylformamide, and then 21.5 ml of 1-bromo-4-chlorobutane.

The mixture is stirred for 5 h at room temperature; 400 ml of water and 400 ml of ether are added, and the organic phase is separated off, washed three times with 50 ml of water and then with 25 ml of saturated sodium chloride solution, dried over magnesium sulphate and evaporated under vacuum. 54.5 g of syrupy product are obtained, and this is used without further treatment in the following stage.

(b)
N-[4-(Dimethylamino)butyl]-N-[2-(2-methylpropoxy)-phenyl]acetamide

The above product is dissolved in 120 ml of dimethylformamide, and 117 g of potassium carbonate, 20 g of potassium iodide, 3 g of tetra-n-butylammonium iodide and 69 g of dimethylamine hydrochloride are added.

The mixture is stirred for 13 h at 70° C. and filtered, washing the solid three times with 200 ml of ether; the filtrate is treated with 400 ml of 0.1 N sodium hydroxide, and the organic phase is separated off, washed three times with 100 ml of water and then with 50 ml of saturated sodium chloride solution, dried over magnesium sulphate and evaporated under vacuum. 42.1 g of syrupy product are obtained, and this is used without further treatment in the following stage.

(c)
N,N-Dimethyl-N'-[2-(2-methylpropoxy)phenyl]-1,4-butanediamine

The above product is dissolved in 280 ml of tetrahydrofuran, 4.9 ml of water and 92.4 g of potassium tertbutylate are added and the mixture is heated to reflux for 12 h. 200 ml of ice-cold water and 600 ml of ether are added, and the organic phase is separated off, washed four times with 100 ml of water and then with 50 ml of saturated sodium chloride solution, dried over magnesium sulphate and evaporated under vacuum. After distillation of the residue under vacuum, 27.1 g of product are obtained.

Boiling point: 106°–110° C. at 13 Pa (0.1 mmHg).

(d)
N-[4-(Dimethylamino)butyl]-N-[2-(2-methylpropoxy)-phenyl]-3-(trifluoromethyl)benzamide A suspension of 5.0 g of the above product and 10.1 g of potassium carbonate in 60 ml of dichloromethane is prepared and is cooled in an ice-bath, and a solution of 3.4 ml of 3-(trifluoromethyl)benzoyl chloride in 60 ml of dichloromethane is added.

The mixture is stirred overnight at room temperature, the solvent is evaporated off, the residue is taken up with 200 ml of ether and 100 ml of water, and the organic phase is separated off, washed three times with 100 ml of water and then with 100 ml of saturated sodium chloride solution, dried over magnesium sulphate and evaporated. The residue is purified by chromatography on a silica column and 6.4 g of syrupy product are obtained.

6.3 g of this are dissolved in 145 ml of a 0.1 N solution of hydrochloric acid in isopropyl alcohol, the solution is evaporated under vacuum and the residue is recrystallized in an ethanol/diisopropyl ether mixture. 5.2 g of hydrochloride are obtained in the form of a white powder. Melting point: 146°–148° C.

EXAMPLE 3

(Compound No. 37)

N-[4-{[2-(3,4-Dimethoxyphenyl)ethyl]methylamino}butyl]-N-[2-(2-methylpropoxy)phenyl]-3-(trifluoromethyl)benzamide oxalate (a)
N-[2-(2-Methylpropoxy)phenyl]-3-(trifluoromethyl)benzamide A solution of 12.5 g of 3.(trifluoromethyl)benzoyl chloride in 60 ml of dichloromethane is added dropwise to a suspension of 9.9 g of 2-(2-methylpropoxy)benzenamine and 33 g of potassium carbonate in 90 ml of dichloromethane, cooled in an ice-bath.

The mixture is stirred overnight at room temperature and the solvent is then evaporated off. The residue is taken up with a mixture of 200 ml of water and 300 ml of ether, and the organic phase is separated off washed successively with twice 50 ml of water, twice 50 ml of 1 N aqueous hydrochloric acid, three times 50 ml of water and 25 ml of saturated sodium chloride solution. It is dried over magnesium sulphate and evaporated under vacuum. 19.7 g of syrupy product are obtained, and this is used without further treatment in the following stage.

(b)
N-(4-Chlorobutyl)-N-[2-(2-methylpropoxy)phenyl]-3-(trifluoromethyl)benzamide To a suspension of 4 g of lithium hydride (at a concentration of 50% in oil) in a 80 ml of dimethylformamide, cooled in an ice-bath, there are added dropwise the 19.7 g of the above product dissolved in 30 ml of dimethylformamide, and then 7.95 ml of 1-bromo-4-chlorobutane.

The mixture is stirred overnight at room temperature, 250 ml of water and 250 ml of ether are then added, the organic phase is separated off, the aqueous phase is extracted a second time with 250 ml of ether, the organic phases are combined to a single phase, and the latter is washed with 100 ml of water, then twice with 100 ml of 0.5 N aqueous hydrochloric acid, then three times with 50 ml of water and finally with 50 ml of saturated sodium chloride solution. It is dried over magnesium sulphate and evaporated under vacuum. 24.2 g of syrupy product are obtained, and this is used without further treatment in the following stage.

(c)
N-[4-{[2-(3,4-Dimethoxyphenyl]methylamino}butyl]-N-[2-(2-methylpropoxy)phenyl]-3-(trifluoromethyl)benzamide A mixture of 2.14 g of the above product, 1.46 g of N-[2-(3,4-dimethoxyphenyl)ethyl]methylamine, 2.07 g of potassium carbonate, 0.8 g of potassium iodide and 0.09 g of tetra-n-butylammonium iodide in 25 ml of dimethylformamide is stirred at 80° C. for 12 h.

250 ml of ether and 50 ml of 0.5 N sodium hydroxide are then added, and the organic phase is separated off, washed three times with 50 ml of water and then with 25 ml of saturated sodium chloride solution, dried over magnesium sulphate and evaporated. The residue is purified by chromatography on a silica column and 2.4 g of syrupy product are obtained.

2.15 g of this are dissolved in 150 ml of ether and a solution of 0.33 g of oxalic acid in 50 ml of ether is added dropwise.

The mixture is left standing overnight at room temperature, and the precipitate is separated off by filtration, washed with ether and recrystallized in a mixture of 40 ml of isopropyl alcohol and 260 ml of diisopropyl ether.

1.6 of oxalate are obtained in the form of a white powder.

Melting point: 80°–82° C.

The table below illustrates the structures and physical properties of a few compounds according to the invention.

TABLE

| Compound | $R_1$ | X | Ar | $R_2$ | $R_3$ | Salt | M.p. (°C.) |
| --- | --- | --- | --- | --- | --- | --- | --- |
| 1 | $-CH_2CH(CH_3)_2$ | H | $C_6H_5$ | $CH_3$ | $CH_3$ | 08 | 110–113 |
| 2 | $-CH_2CH(CH_3)_2$ | H | $C_6H_4$-3-$CF_3$ | $CH_3$ | $CH_3$ | 10 | 146–148 |
| 3 | $-CH_2CH(CH_3)_2$ | 4-F | $C_6H_4$-3-$CF_3$ | $CH_3$ | $CH_3$ | 10 | 119–120 |
| 4 | $-CH_2CH(CH_3)_2$ | 5-Cl | $C_6H_4$-3-$CF_3$ | $CH_3$ | $CH_3$ | 46 | 124–130 |
| 5 | $-CH_2C(CH_3)_3$ | H | $C_6H_4$-3-$CF_3$ | $CH_3$ | $CH_3$ | 46 | 116–120 |
| 6 | $-CH_2$-$cC_3H_5$ | H | $C_6H_4$-3-$CF_3$ | $CH_3$ | $CH_3$ | 10 | 118–120 |
| 7 | $-CH_2$-$cC_5H_9$ | H | $C_6H_4$-3-$CF_3$ | $CH_3$ | $CH_3$ | 10 | 142–144 |
| 8 | $-CH(CH_3)_2$ | H | $C_6H_4$-3-$CF_3$ | $CH_3$ | $CH_3$ | 10 | 134–136 |
| 9 | -$cC_5H_9$ | H | $C_6H_4$-3-$CF_3$ | $CH_3$ | $CH_3$ | 10 | 110–112 |
| 10 | $-CH_2CH(CH_3)_2$ | H | $C_6H_4$-2-F | $CH_3$ | $CH_3$ | 46 | 111–114 |
| 11 | $-CH_2CH(CH_3)_2$ | H | $C_6H_4$-2-Cl | $CH_3$ | $CH_3$ | 08 | 144–146 |
| 12 | $-CH_2CH(CH_3)_2$ | H | $C_6H_4$-2-$OCH_3$ | $CH_3$ | $CH_3$ | 08 | 150–152 |
| 13 | $-CH_2CH(CH_3)_2$ | H | $C_6H_4$-3-$NO_2$ | $CH_3$ | $CH_3$ | 46 | 146–148 |
| 14 | $-CH_2CH(CH_3)_2$ | H | $C_6H_4$-2-$NO_2$ | $CH_3$ | $CH_3$ | 46 | 112–114 |
| 15 | $-CH_2CH(CH_3)_2$ | H | $C_6H_4$-3-F | $CH_3$ | $CH_3$ | 10 | 122 |
| 16 | $-CH_2CH(CH_3)_2$ | H | $C_6H_4$-3-Cl | $CH_3$ | $CH_3$ | 10 | 135–136 |
| 17 | $-CH_2CH(CH_3)_2$ | H | $C_6H_4$-2-$CF_3$ | $CH_3$ | $CH_3$ | 46 | 133–134 |
| 18 | $-CH_2CH(CH_3)_2$ | H | $C_6H_4$-2-CN | $CH_3$ | $CH_3$ | 10 | 144–146 |
| 19 | $-CH_2CH(CH_3)_2$ | H | $C_6H_3$-2,3-$(CH_3)_2$ | $CH_3$ | $CH_3$ | 46 | 138–140 |
| 20 | $-CH_2CH(CH_3)_2$ | H | $C_6H_3$-2-$CH_3$-3-$NO_2$ | $CH_3$ | $CH_3$ | 46 | 148–150 |
| 21 | $-CH_2CH(CH_3)_2$ | H | $C_6H_3$-2-Cl-3-$NO_2$ | $CH_3$ | $CH_3$ | 08 | 114–116 |
| 22 | $-CH_2CH(CH_3)_2$ | H | $C_6H_3$-2,3-$Cl_2$ | $CH_3$ | $CH_3$ | 08 | 154–156 |
| 23 | $-CH_2CH(CH_3)_2$ | H | $C_6H_3$-2,5-$Cl_2$ | $CH_3$ | $CH_3$ | 08 | 130 |
| 24 | $-CH_2CH(CH_3)_2$ | H | $C_6H_3$-2-Cl-6-F | $CH_3$ | $CH_3$ | 08 | 152–154 |

TABLE-continued

| Compound | R₁ | X | Ar | R₂ | R₃ | Salt | M.p. (°C.) |
|---|---|---|---|---|---|---|---|
| 25 | —CH₂CH(CH₃)₂ | H | C₆H₃-2-Cl-4-NO₂ | CH₃ | CH₃ | 10 | 190–192 |
| 26 | —CH₂CH(CH₃)₂ | H | C₆H₃-2-Cl-5-NO₂ | CH₃ | CH₃ | 10 | 166–168 |
| 27 | —CH₂CH(CH₃)₂ | H | C₆H₃-2,4-Cl₂ | CH₃ | CH₃ | 10 | 180–182 |
| 28 | —CH₂CH(CH₃)₂ | H | C₆H₃-2-NO₂-5-Cl | CH₃ | CH₃ | 10 | 140–142 |
| 29 | —CH₂CH(CH₃)₂ | H | C₆H₃-2-OCH₃-5-NO₂ | CH₃ | CH₃ | 10 | 126–130 |
| 30 | —CH₂CH(CH₃)₂ | H | C₆H₃-2-Cl-5-Br | CH₃ | CH₃ | 10 | 186–188 |
| 31 | —CH₂CH(CH₃)₂ | H | C₆H₃-3,5-Cl₂ | CH₃ | CH₃ | 46 | 156–158 |
| 32 | —CH₂CH(CH₃)₂ | H | C₆H₃-3-NO₂-4-Cl | CH₃ | CH₃ | 46 | 114–116 |
| 33 | —CH₂CH(CH₃)₂ | H | C₆H₃-3,4-Cl₂ | CH₃ | CH₃ | 46 | 139–141 |
| 34 | —CH₂CH(CH₃)₂ | H | C₆H₅ | —(CH₂)₄— | | 46 | 110–112 |
| 35 | —CH₂CH(CH₃)₂ | H | C₆H₄-4-OCH₃ | —(CH₂)₄— | | 46 | 149 |
| 36 | —CH₂CH(CH₃)₂ | H | C₆H₄-3-CF₃ | 4-phenylcyclohexylidene (R₂/R₃ together = —(CH₂)₂CH(C₆H₅)(CH₂)₂—) | | 46 | 134–136 |
| 37 | —CH₂CH(CH₃)₂ | H | C₆H₄-3-CF₃ | CH₃ | CH₂CH₂-(3,4-dimethoxyphenyl) | 46 | 80–82 |
| 38 | —CH₂CH(CH₃)₂ | H | C₆H₄-3-CF₃ | CH₃ | CH₂CH₂-(2-pyridyl) | 2.10 | 146–149 |
| 39 | —CH₂CH(CH₃)₂ | H | C₆H₄-3-CF₃ | CH₃ | CH₂C₆H₅ | 46 | 160–162 |
| 40 | —CH₂CH(CH₃)₂ | H | C₆H₄-3-CF₃ | R₂/R₃ together: fused 4,5-dimethoxy-1,2-phenylene-bis(ethylene) (tetrahydroisoquinoline-type) | | 15 | 142–144 |
| 41 | —CH₂CH(CH₃)₂ | H | 1-naphthyl | CH₃ | CH₃ | 46 | 178–180 |
| 42 | —CH₂CH(CH₃)₂ | H | 1-isoquinolinyl | CH₃ | CH₃ | 46 | 120–122 |
| 43 | —CH₂CH(CH₃)₂ | H | 4-quinolinyl | CH₃ | CH₃ | 46 | 146–148 |
| 44 | —CH₂CH(CH₃)₂ | 4-CH₃ | 1-naphthyl | CH₃ | CH₃ | ½08 | 150–151 |
| 45 | —CH₂CH(CH₃)₂ | 4-F | 1-naphthyl | CH₃ | CH₃ | ½08 | 174–176 |
| 46 | —CH₂CH(CH₃)₂ | 5-Cl | 1-naphthyl | CH₃ | CH₃ | 10 | 104–108 |
| 47 | —CH₂CH(CH₃)₂ | 4-OCH₃ | 1-naphthyl | CH₃ | CH₃ | ½08 | 152–154 |
| 48 | —CH₂CH(CH₃)₂ | 5-CH₃ | 1-naphthyl | CH₃ | CH₃ | 46 | 114–118 |
| 49 | —CH₂CH(CH₃)₂ | 5-CF₃ | 1-naphthyl | CH₃ | CH₃ | 46 | 156–158 |
| 50 | —CH₂CH(CH₃)₂ | H | 1-naphthyl | C₃H₇ | C₃H₇ | 10 | 120 |
| 51 | —CH₂CH(CH₃)₂ | H | 1-naphthyl | —(CH₂)₅— | | 10 | 198–200 |
| 51a | —CH₂CH(CH₃)₂ | H | 2-naphthyl | CH₃ | CH₃ | 08 | 152–154 |
| 51b | —CH₂CH(CH₃)₂ | H | 3-pyridyl | CH₃ | CH₃ | 10 | 104–106 |
| 52 | —CH₂CH(CH₃)₂ | H | 1-naphthyl | morpholino (R₂+R₃ = —(CH₂)₂O(CH₂)₂—) | | 10 | 188–190 |
| 53 | —CH₂CH(CH₃)₂ | H | 1-naphthyl | thiomorpholino (R₂+R₃ = —(CH₂)₂S(CH₂)₂—) | | 10 | 214–216 |
| 54 | —CH₂CH(CH₃)₂ | H | 1-naphthyl | N-methylpiperazino (R₂+R₃ = —(CH₂)₂N(CH₃)(CH₂)₂—) | | 10 | 110–120 |
| 55 | —CH₂CH(CH₃)₂ | H | 1-naphthyl | CH₃ | CH₂CH₂-(3,4-dimethoxyphenyl) | 46 | 87–93 |

TABLE-continued
| Compound | R₁ | X | Ar | R₂ | R₃ | Salt | M.p. (°C.) |
|---|---|---|---|---|---|---|---|
| 56 | —CH₂CH(CH₃)₂ | H | C₆H₃-2-Cl-5-NO₂ | CH₃ | 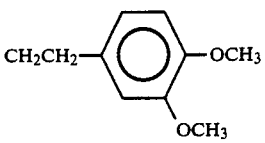 | 46 | 143–145 |
| 57 | —CH₂CH(CH₃)₂ | H | C₆H₄-3-CF₃ | CH₃ | 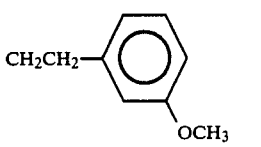 | 46 | 136–138 |
| 58 | —CH₂CH(CH₃)₂ | H | C₆H₄-3-CF₃ | CH₃ | 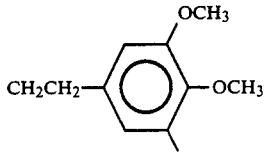 | 10 | 151–153 |
| 59 | —CH₂CH(CH₃)₂ | H | C₆H₄-4-CF₃ | CH₃ | 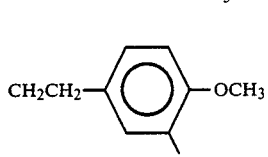 | 46 | 128–130 |
| 60 | —CH₂CH(CH₃)₂ | H | C₆H₃-2-OCH₃-5-NO₂ | CH₃ | 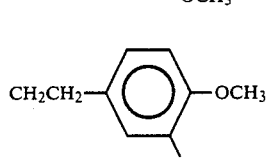 | 10 | 158–160 |
| 61 | —CH₂CH(CH₃)₂ | H | C₆H₃-2,5-Cl₂ | CH₃ | 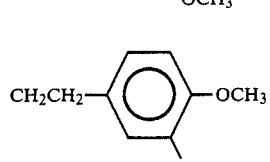 | 10 | 78–80 |
| 62 | —CH₂CH(CH₃)₂ | H | C₆H₃-2-CH₃-3-NO₂ | CH₃ | 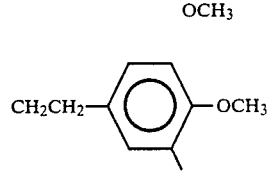 | 10 | 104–106 |
| 63 | —CH₂CH(CH₃)₂ | H | C₆H₃-3,4-(OCH₃)₂ | CH₃ | 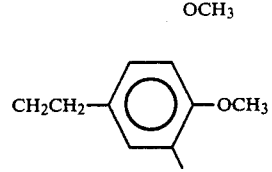 | 46 | 81–83 |
| 64 | —CH₂CH(CH₃)₂ | H | C₆H₃-3,4-OCH₂O— | CH₃ | 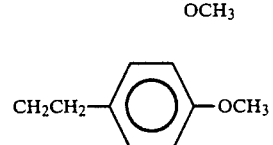 | 46 | 133–134 |
| 65 | —CH₂CH(CH₃)₂ | H | C₆H₂-3,4,5-(OCH₃)₃ | CH₃ | 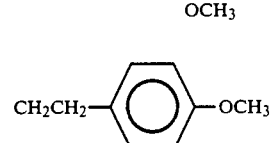 | 46 | 90–94 |

TABLE-continued
| Compound | R₁ | X | Ar | R₂ | R₃ | Salt | M.p. (°C.) |
|---|---|---|---|---|---|---|---|
| 66 | —CH₂CH(CH₃)₂ | H | C₆H₄-3-NO₂ | CH₃ | 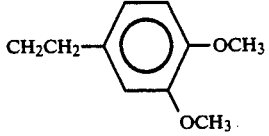 | 10 | 120–122 |
| 67 | —CH₂CH(CH₃)₂ | H | C₆H₃-2,3-(CH₃)₂ | CH₃ | 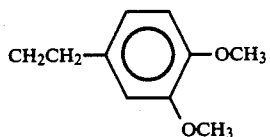 | 46 | 80–84 |
| 68 | —CH₂CH(CH₃)₂ | H | C₆H₃-2,3-Cl₂ | CH₃ | 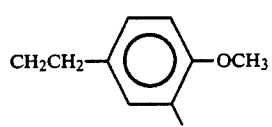 | 46 | 98–100 |
| 69 | —CH(CH₃)₂ | H | C₆H₄-3-CF₃ | CH₃ | 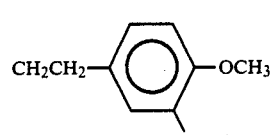 | 46 | 115–117 |
| 70 | —C(CH₂)₃ | H | C₆H₄-3-CF₃ | CH₃ | 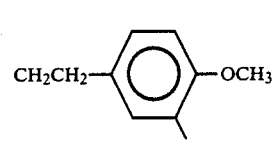 | 46 | 128–130 |
| 71 | -cC₅H₉ | H | C₆H₄-3-CF₃ | CH₃ | 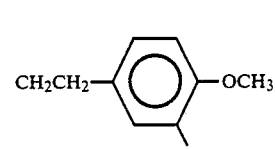 | 46 | 132–134 |
| 72 | —CH₂CH(CH₃)₂ | H | C₆H₄-3-CF₃ | H | 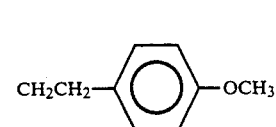 | 08 | 132–134 |
| 73 | —CH₂CH(CH₃)₂ | H | C₆H₄-3-CF₃ | CH₃ | 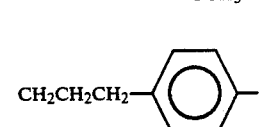 | 46 | 66–70 |
| 74 | —CH₂CH(CH₃)₂ | H | C₆H₄-3-CF₃ | CH₃ | 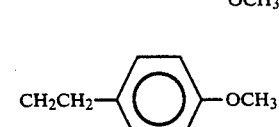 | 46 | 122–124 |
| 75 | —CH₂CH(CH₃)₂ | H | C₆H₄-3-CF₃ | CH₃ | 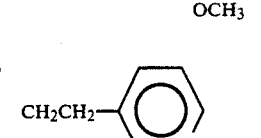 | 2.46<br>2.10 | 112–116<br>140–150 |

TABLE-continued

| Compound | R₁ | X | Ar | R₂ | R₃ | Salt | M.p. (°C.) |
|---|---|---|---|---|---|---|---|
| 76 | —CH₂CH(CH₃)₂ | H | C₆H₄-3-CF₃ | CH₃ | 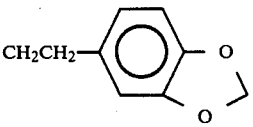 | 10 | 138–140 |
| 77 | —CH₂CH(CH₃)₂ | H | C₆H₄-3-CF₃ | CH₃ | 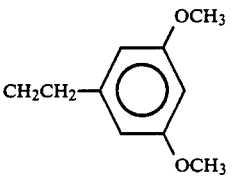 | 46 | 122–124 |
| 78 | —CH₂CH(CH₃)₂ | H | C₆H₄-3-CF₃ | CH₃ | 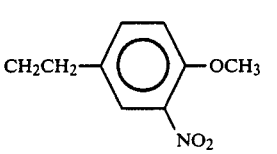 | 46 | 104–108 |
| 79 | —CH₂CH(CH₃)₂ | H | C₆H₄-3-CF₃ | CH₃ | 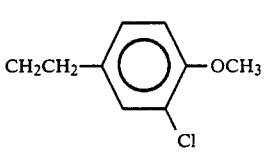 | 10 | 120–124 |
| 80 | —CH₂CH(CH₃)₂ | H | C₆H₄-3-CF₃ | CH₃ | 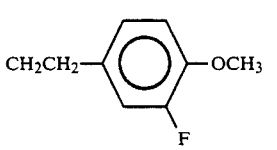 | 10 | 114–118 |
| 81 | —CH₂CH(CH₃)₂ | H | C₆H₄-3-CF₃ | CH₃ | 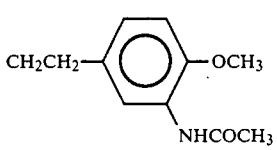 | 46 | 88–90 |

Legend to the table
"R1" column: cC₃H₅ and cC₅H₉ denote cyclopropyl and cyclopentyl groups, respectively.
"Ar" column: C₆H₅, C₆H₄, C₆H₃ and C₆H₂ denote unsubstituted, monosubstituted, disubstituted and trisubstituted phenyl groups, respectively. The formulae of these substituents are shown, preceded by their positional number(s).
"Salt" column:
08 denotes the fumarate
½08 denotes the hemifumarate
10 denotes the hydrochloride
2.10 denotes the dihydrochloride
15 denotes the methanesulphonate
46 denotes the oxalate
2.46 denotes the dioxalate The compounds of the invention were subjected to various pharmacological tests to demonstrate their therapeutic activity.

Thus, for example, their antagonistic action towards the effects of calcium was studied on isolated rabbit aorta.

The experimental protocol used is a variant of that of Godfraind and Kaba [Blockade or reversal of the contraction induced by calcium and adrenaline in depolarized arterial smooth muscle, Br. J. Pharmac., (1969), 36, 549–560]. The experiments were carried out on sections of rabbit thoracic aorta. The animals, "Fauves de Bourgogne" weighing on average 1.5 kg, were sacrificed by cervical dislocation and exsanguination. The thoracic aorta was rapidly removed and placed in an oxygenated Krebs bicarbonate medium (95% $O_2$ + 5% $CO_2$).

Sections of aorta approximately 1 cm long were prepared and installed in 20-ml organ cells containing oxygenated Krebs bicarbonate solution at pH 7.4 at 37° C. Two U-shaped metal hooks having the same length as the sections were introduced into the bore of aorta sections. One of the hooks was attached to the base of the cell and the other, connected to an isometric strain gauge (Grass FTO3), permitted the recording, via a continuous preamplifier (Grass 7P1), of the contractile responses of the sections of aorta on a pen oscillograph (Grass 79B). Compared with spiral or ring-shaped preparations, this method has the advantage of having greater regard for the structural integrity of the vessels, and of recording only the radical component of the contractile responses, which represents the phenomenon of interest from the functional standpoint (regulation of arterial blood pressure). An initial tension of 4 g was applied to the preparations.

Phenoxybenzamine (1 µM) and propranolol (1 µM) were added to the different Krebs media to abolish the contractile responses linked to the activation of the vascular α- and β-adrenergic receptors.

After one hour's stabilization in the Krebs medium, the tension applied to the aorta sections was reduced to 2 g, and then, after a delay of 30 minutes, the preparations were incubated for about 10 minutes in a Krebs bicarbonate solution without calcium in the presence of EDTA (200 µM) and propranolol (1 µM). This solution was then replaced by a depolarizing Krebs medium (rich in potassium) without calcium and containing propranolol (1 µM). After 5 minutes, a single concentration of 1 mM of calcium was added to this solution and a stabilization period of 30 minutes was observed, which enables the preparations to achieve stable contraction.

Cumulative doses of the test compounds were then administered every 30 minutes (the time generally necessary for obtaining a plateau), until there was complete disappearance of the contraction induced by 1 mM calcium, or alternatively, until a 30 µM concentration of the test product was obtained.

At the end of the experiment, a supramaximal concentration of papaverine (300 µM) was administered to determine the maximum possible relaxation of each preparation.

The absolute values (in grams) of the initial contraction (after 1 mM calcium chloride) and of the contraction after the different cumulative concentrations of vasodilatory compounds were obtained, for each preparation, by their differences with the minimal contraction observed 30 minutes after the final addition of 300 µM papaverine. The percentage decrease in the contraction, relative to the contraction induced by 1 mM calcium, was calculated for each dose of compound and each preparation, and the mean $\bar{X}\pm SEM$ of the individual percentages was calculated. The means obtained (weighted by the reciprocal of the standard error of the mean) were analyzed using a mathematical sigmoid curve model, and the molar concentration inducing 50% relaxation of the response to calcium ($EC_{50}$) was calculated.

For the compounds of the invention the $EC_{50}$ values generally are from 0.2 to 10 µM.

The compounds of the invention were also subjected to a test of binding [$^3$H]nitrendipine to whole rat cortex.

Sprague-Dawley male rats weighing 150 to 200 g were used. After cervical dislocation, the brain was excized and the cerebral cortex dissected on a culture dish in ice. It was placed in 20 volumes of an ice-cold 50 mM tris(hydroxymethyl)aminomethane buffer solution whose pH had been adjusted to 7.4 with hydrochloric acid ("Tris-HCl" buffer). The tissue was homogenized using a Polytron Ultra-Turrax apparatus for 30 seconds at one half maximum speed, and the preparations were washed three times with the ice-cold buffer solution, draining them each time by centrifugation at 49,000×g for 10 minutes. Finally, suspensions were prepared containing 100 mg of tissue in 1 ml of 30 mM Tris-HCl buffer (pH 7.4 at 37° C.)

100-µl aliquot portions of the suspension of washed membranes were then incubated with [$^3$H]nitrendipine (New England Nuclear, specific activity 70.0 Ci/mmol) in a final volume of 1 ml of Tris-HCl buffer. After 30 minutes' incubation at 37° C., the membranes were recovered by filtration on Whatman GF/F glass fibres, and washed three times with 5 ml of ice-cold Tris-HCl buffer. The quantity of radioactivity bound to the tissue and retained on the filters was measured by scintillation spectrometry. The specific binding of [$^3$H]nitrendipine is defined as the decrease in the quantity of radioligand retained on the filter due to the introduction of 1 µM nifedipine during the incubation. The specific binding represents 80 to 90% of the total quantity of radioactivity collected on the filter. Using different concentrations of test compounds, the $IC_{50}$ concentration, the concentration of the test compounds which inhibits 50% of the specific binding of [$^3$H]nitrendipine was determined graphically.

The $IC_{50}$ concentrations of the compounds of the invention generally are from 0.005 to 0.1 µM.

Finally, the compounds of the invention were studied in respect of their antihypertensive effect in spontaneously hypertensive rats.

The systolic pressure was measured by means of a catheter placed in the caudal artery, according to the method of Gerold and Tschirky (Arzneim.-Forsch., 1968 18, 1285-1287), and the pressure changes were recorded in terms of the time elapsed, for each test compound and for each dose administered. The compounds of the invention produce a decrease in the blood pressure of 15 to 30% after 30 minutes, and of 20 to 25% after 3 hours, at doses of 5 to 30 mg/kg administered intraperitoneally.

The results of the pharmacological tests show that the compounds of the invention are calcium antagonists, and they can, on this ground, be used for the treatment of various conditions for which this type of agent is indicated.

Thus, in particular, they may be used in cardiovascular medicine for the treatment of conditions requiring modulators of the transmembraneous and intracellular movements of calcium, most especially hypertension, angina and cardiac arrhythmia.

They may, in addition, possess anti-atherogenic, platelet-aggregation inhibitory, cardiac-anti-ischaemic, cerebral anti-ischaemic, antimigraine, antiepileptic, anti-asthmatic and antiulcer effects. In the cardiovascular field, they may be used alone or in combination with other known active substances such as diuretics, β-blockers, angiotensin-converting enzyme inhibitors and $\alpha_1$-receptor antagonists.

In combination with agents designed to boost their effects or decrease their toxicity, they may also be indicated for the treatment of cancer or in transplantation.

The compounds of the invention may be presented in any form suitable for oral or parenteral administration, in combination with known excipients, for example in the form of tablets, gelatin capsules, dragees, capsules, and solutions or suspensions to be taken by mouth or injected.

The daily dosage can range, for example, from 5 to 200 mg orally and from 0.1 to 10 mg parenterally.

We claim:

1. A compound of formula (I)

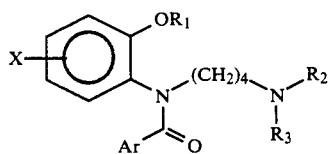

wherein:

X is selected from the group of substituents consisting of a hydrogen, a halogen, a trifluoromethyl group, a $C_1$-$C_4$ alkyl group and a $C_1$-$C_4$ alkoxy group;

$R_1$ is selected from the group of substituents consisting of a liner or branched $C_2$-$C_8$ alkyl group, a $C_3$-$C_5$ cycloalkyl group and a cycloalkylmethyl group in which the cycloalkyl moiety has from 3 to 5 carbon atoms;

$R_2$ is hydrogen or a $C_1$-$C_4$ alkyl group;

$R_3$ is selected from the group consisting of hydrogen, a $C_1$-$C_4$ alkyl group, an unsubstituted phenylalkyl group, and a phenylalkyl group substituted with at least one substituent; wherein said substituent on said phenylalkyl group is selected from the group consisting of a methoxy group, a methylenedioxy group, a nitro group, a fluoro, a chloro and an acetylamino group; and Ar is a phenyl group that is unsubstituted or is substituted with from one to three substituents, each of which is, independently, a halogen or a $C_1$-$C_4$ alkyl, $C_1$-$C_4$ alkoxy, trifluoromethyl, nitro or cyano group or Ar is a naphthyl group;

or a pharmacologically acceptable acid addition salt thereof.

2. A compound according to claim 1 wherein $R_1$ denotes an isobutyl group and Ar denotes a substituted phenyl group.

3. A compound according to claim 2 wherein X denotes hydrogen and $R_2$ denotes a methyl group.

4. A compound according to claim 3 wherein $R_3$ denotes a methyl group and Ar denotes a 2,3-dimethylphenyl group.

5. A compound according to claim 3 wherein $R_3$ denotes a methyl group and Ar denotes a 3-trifluoromethylphenyl group.

6. A compound according to claim 3 wherein $R_3$ denotes a methyl group and Ar denotes a 3-nitrophenyl group.

7. A compound according to claim 3 wherein $R_3$ denotes a methyl group and Ar denotes a 2-methoxy-5-nitrophenyl group.

8. N-[4-{[2-(3-methoxy phenyl)ethyl]methyl amino} butyl]-N-[2-(2-methyl propoxy)phenyl]-3-(trifluoromethyl) benzamide.

9. N-[4-{[2-(3,4-dimethoxy phenyl)ethyl]methyl amino}-butyl]-N-[2-(2-methyl-propoxy)phenyl]-3-(trifluoromethyl) benzamide.

10. A compound according to claim 3 wherein Ar denotes a 3-trifluoromethylphenyl group.

11. N-[4-2-(3,4-dimethoxy phenyl)ethyl]methylamino butyl]-N-[2-(2-methyl-propoxy)phenyl]-2-methyl-3-nitro benzamide.

12. A pharmaceutical composition comprising a compound of formula (I) as defined in claim 1 and a pharmaceutical excipient.

13. A method of treatment of hypertension, angina, atherosclerosis, platelet-aggregation, cardia arrhythmia, cardiac ischamia, cerebral ischaemia, migraines, epilepsy, asthma, ulcer or which comprises administering to a subject in need of such treatment an effective amount of a compound as defined in claim 1.

14. A compound according to claim 1 wherein $R_3$ is a phenylalkyl group substituted by methoxy.

15. A compound according to claim 1 wherein $R_3$ is a phenylalkyl group substituted by $NO_2$.

16. A compound according to claim 1 wherein $R_3$ is a phenylalkyl group substituted by Cl or F.

17. A compound according to claim 1 wherein $R_3$ is a phenylalkyl group substituted by $NHCOCH_3$.

* * * * *